(12) United States Patent
Yi et al.

(10) Patent No.: US 12,251,235 B2
(45) Date of Patent: Mar. 18, 2025

(54) PERSPIRATION MAPPING PATCH

(71) Applicant: KOREA INSTITUTE OF SCIENCE AND TECHNOLOGY, Seoul (KR)

(72) Inventors: Hyunjung Yi, Seoul (KR); Seongjin Park, Seoul (KR); Wonseop Hwang, Seoul (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 720 days.

(21) Appl. No.: 17/507,811

(22) Filed: Oct. 22, 2021

(65) Prior Publication Data
US 2023/0055053 A1 Feb. 23, 2023

(30) Foreign Application Priority Data
Aug. 20, 2021 (KR) .................. 10-2021-0109877

(51) Int. Cl.
*A61B 5/00* (2006.01)
*A61B 10/00* (2006.01)
(Continued)

(52) U.S. Cl.
CPC .......... *A61B 5/4266* (2013.01); *A61B 5/6833* (2013.01); *A61B 10/0064* (2013.01);
(Continued)

(58) Field of Classification Search
CPC ............ A61B 5/14517; A61B 5/14532; A61B 5/14546; A61B 5/1486; A61B 5/6801; A61B 10/0064; A61B 5/6833; A61B 5/1477; A61B 5/4266; G01N 27/3271; G01N 27/333; G01N 27/4145; A61F 13/02; A61F 13/0203; A61F 13/0206; A61F 13/0209; A61F 13/15; A61F 13/53; A61F 2013/530255; A61F 2013/530788
See application file for complete search history.

(56) References Cited

U.S. PATENT DOCUMENTS 4,245,630 A * 1/1981 Lloyd ..................... A61L 15/58
 604/358
4,979,946 A * 12/1990 Gilman ............... A61F 13/0226
 602/57
(Continued)

FOREIGN PATENT DOCUMENTS

CN 208710260 U 4/2019
JP 2014168573 A 9/2014
(Continued)

OTHER PUBLICATIONS

Machine Translation of JP 2014168573 (Year: 2014).*

*Primary Examiner* — David J. McCrosky
(74) *Attorney, Agent, or Firm* — CANTOR COLBURN LLP

(57) ABSTRACT

A perspiration mapping patch according to the present disclosure is attached to skin of a user to absorb sweat, and includes: a sweat absorbing layer in which a plurality of opening units is arranged; a first support layer which is stacked on a first surface of the sweat absorbing layer and includes an opening opened to correspond to each of the plurality of opening units; and a second support layer stacked on a second surface facing an opposite side of the first surface of the sweat absorbing layer.

17 Claims, 18 Drawing Sheets

(51) Int. Cl.
*A61F 13/15* (2006.01)
*A61F 13/53* (2006.01)

(52) U.S. Cl.
CPC ........ *A61F 13/15203* (2013.01); *A61F 13/53* (2013.01); *A61F 2013/530255* (2013.01); *A61F 2013/530788* (2013.01)

(56) References Cited

U.S. PATENT DOCUMENTS

| | | | |
|---|---|---|---|
| 10,479,852 | B2 | 11/2019 | Kim et al. |
| 2010/0191148 | A1* | 7/2010 | Matsumura ........ A61B 5/15109 600/583 |
| 2014/0275862 | A1 | 9/2014 | Kennedy |
| 2017/0296114 | A1 | 10/2017 | Ghaffari et al. |
| 2020/0205673 | A1 | 7/2020 | Yi et al. |
| 2024/0225618 | A1* | 7/2024 | Garnier .............. A61B 5/14517 |

FOREIGN PATENT DOCUMENTS

| | | |
|---|---|---|
| KR | 10-1649480 B1 | 8/2016 |
| KR | 10-1649547 B1 | 8/2016 |
| KR | 10-2016-0108054 A | 9/2016 |
| KR | 10-2206105 B1 | 1/2021 |
| WO | 2017/218878 A1 | 12/2017 |
| WO | 2019/185270 A1 | 10/2019 |

* cited by examiner

PERSPIRATION MAPPING PATCH

CROSS-REFERENCE TO RELATED APPLICATION

This application claims priority to and the benefit of Korean Patent Application No. 10-2021-0109877 filed in the Korean Intellectual Property Office on Aug. 20, 2021, the entire contents of which are incorporated herein by reference.

BACKGROUND OF THE INVENTION

(a) Field of the Invention

The present disclosure relates to a perspiration mapping patch used while being attached to skin of a user.

(b) Description of the Related Art

Customized technology that measures biometric information non-invasively and long-term efficiently manages personal health and adopts the measured biometric information to treatment based on the biometric information is in the spotlight as a technology that can change the paradigm of the future medical and health care industry. Recently, in particular, research on a skin-attached sensor which is attached to skin to monitor a bio-signal is also being actively conducted. The bio-signal provides important information for biomedical devices, and multiple biosensors are essentially required to obtain individual signals from multiple points in a wide area.

However, a size of an area (hole) in which sweat is collected is generally very small compared to an entire size of the device of the perspiration sensor patch. Further, a location at which the amount of sweat secretion is large may be different depending on each person and each body region of a person. Accordingly, efficiency of collecting sweat and an analysis result may be different depending on the location where the perspiration sensor patch is attached.

Accordingly, in order to increase the usability and reliability of the sweat perspiration sensor patch, there is a need for a technology to identify and find locations where the amount of sweat secretion is large.

Further, the degree of sweat secretion may vary from person to person, and a health status and an exercise status may be analyzed based on the amount of sweat secretion, and knowing information about the average amount of sweat secretion of each individual may be necessary for efficient operation of a sweat sensor and interpretation of sensor data.

The above information disclosed in this Background section is only for enhancement of understanding of the background of the invention, and therefore it may contain information that does not form the prior art that is already known in this country to a person of ordinary skill in the art.

SUMMARY OF THE INVENTION

The present invention has been made in an effort to provide a perspiration mapping patch configured to recognize or display a location where sweat is secreted well in advance before a perspiration sensor patch is attached to skin.

However, the object to be solved in the exemplary embodiments of the present invention is not limited to the foregoing object, and may be variously extended in the scope of the technical spirit included in the present invention.

An exemplary embodiment of the present invention provides a perspiration mapping patch attached to skin of a user to absorb sweat, the perspiration mapping patch including: a sweat absorbing layer in which a plurality of opening units is arranged; a first support layer which is stacked on a first surface of the sweat absorbing layer and includes an opening opened to correspond to each of the plurality of opening units; and a second support layer stacked on a second surface facing an opposite side of the first surface of the sweat absorbing layer.

Each of the plurality of opening units may include a protrusion extendable in a plane direction The protrusion may be configured to protrude into the opening of the first support layer.

At least one pair of protrusions may be disposed to face each other.

The protrusion may be formed to be tapered as the protrusion approaches a center of each of the opening units.

At least one pair of protrusions extended alternately may be disposed in the opening.

The first support layer may include a material having hydrophobicity.

The first support layer may be configured to have adhesiveness.

The second support layer may include a material having hydrophobicity.

In the second support layer, at least an area corresponding to each of the plurality of opening units may be formed to be transparent.

The plurality of opening units may be formed to have a matrix array.

The first surface of the sweat absorbing layer may be configured to face the skin.

The second support layer may be configured to cover and block the opening unit of the sweat absorbing layer.

The sweat absorbing layer may include a hydrogel.

The sweat absorbing layer may be configured to have a color.

The sweat absorbing layer may include a plurality of unit cells divided for the plurality of opening units, respectively, and the plurality of unit cells may be configured to be perforated from each other, According to the perspiration mapping patch according to the exemplary embodiments, by analyzing a pattern immediately after the patch is attached to the skin and a shape of the deformed pattern after a certain period of time, it is possible to easily analyze the location and the degree of sweating only with a camera and a simple image analysis.

Further, a portion of the patch corresponding to an area where a lot of sweat is partially absorbed may be separated and left on the skin and displayed.

When the degree of sweating is analyzed, it is possible to recognize information about a skin state and physical constitution.

DETAILED DESCRIPTION OF THE EMBODIMENTS

Figure 1:
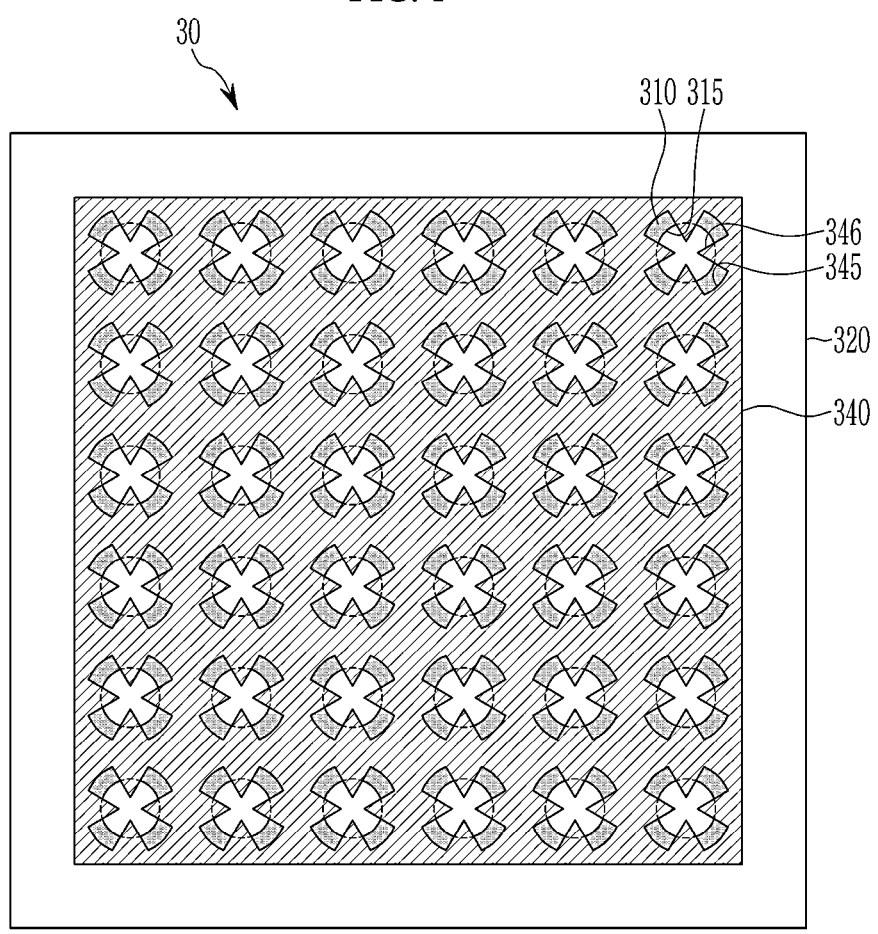
FIG. 1 is a top plan view illustrating a perspiration mapping patch according to an exemplary embodiment.

The present invention will be described more fully hereinafter with reference to the accompanying drawings, in which exemplary embodiments of the invention are shown. The drawings and description are to be regarded as illustrative in nature and not restrictive. Like reference numerals designate like elements throughout the specification. Further, some constituent elements in the accompanying drawings are exaggerated, omitted, or schematically illustrated, and a size of each constituent element does not fully reflect an actual size.

Further, the accompanying drawings are provided for helping to easily understand exemplary embodiments disclosed in the present specification, and the technical spirit disclosed in the present specification is not limited by the accompanying drawings, and it will be appreciated that the present invention includes all of the modifications, equivalent matters, and substitutes included in the spirit and the technical scope of the present invention.

Terms including an ordinary number, such as first and second, are used for describing various constituent elements, but the constituent elements are not limited by the terms. The terms are used only to discriminate one constituent element from another constituent element.

Further, it will be understood that when an element such as a layer, film, region, or substrate is referred to as being "on" another element, it can be directly on the other element or intervening elements may also be present, In contrast, when an element is referred to as being "directly on" another element, there are no intervening elements present. Further, when an element is "on" a reference portion, the element is located above or below the reference portion, and it does not necessarily mean that the element is located "on" in a direction opposite to gravity.

In the present application, it will be appreciated that terms "including" and "having" are intended to designate the existence of characteristics, numbers, steps, operations, constituent elements, and components described in the specification or a combination thereof, and do not exclude a possibility of the existence or addition of one or more other characteristics, numbers, steps, operations, constituent elements, and components, or a combination thereof in advance. In the specification, unless explicitly described to the contrary, the word "comprise" and variations such as "comprises" or "comprising", will be understood to imply the inclusion of stated elements but not the exclusion of any other elements.

Further, throughout the specification, when it is referred to as "planar", it means the case where a target part is viewed from above, and when it is referred to as "in cross-section", it means the case where a cross-section obtained by vertically cutting the target part is viewed from the side.

Further, throughout the specification, when it is referred to as "connected", this does not only mean that two or more constituent elements are directly connected, but may mean that two or more constituent elements are indirectly connected through another constituent element, are physically connected, electrically connected, or are integrated even though two or more constituent elements are referred as different names depending on a location and a function.

FIG. 1 is a top plan view illustrating a perspiration mapping patch according to an exemplary embodiment.

Referring to FIG. 1, a perspiration mapping patch 30 according to an exemplary embodiment is the patch configured to be attached to skin of a user and absorb sweat, and includes a first support layer 310 and a second support layer 320 stacked on both surfaces of a sweat absorbing layer 340, respectively. The sweat absorbing layer 340 is shaped like a sheet and includes a first surface and a second surface which face each other in opposite directions, and the first support layer 310 may be stacked on the first surface and the second support layer 320 may be stacked on the second surface. In this case, the first surface of the sweat absorbing layer 340 is configured to face the skin of the user, and the first support layer 310 may be attached to the skin.

A plurality of opening units 345 is arranged and formed in the sweat absorbing layer 340. The plurality of opening units 345 may be formed to have a matrix array. That is, the plurality of opening units 345 may be arranged in all directions in the plane direction of the sweat absorbing layer 340. Each of the opening units 345 may have a circular, oval, or polygonal planar shape, and a protrusion 346 may be further formed in the opening unit 345. Herein, the "plane direction" may be defined as a direction parallel to the surface of the sweat absorbing layer 340 formed of a sheet shape, and a "thickness direction" may be defined as a direction vertical to the surface of the sweat absorbing layer 340.

The first support layer 310 may include a plurality of openings 315 opened while corresponding to the plurality of opening units 345, respectively. Each opening 315 may have, for example, a circular shape, and the openings 315 may be formed to have a matrix array. The first support layer 310 may include a polymer material having hydrophobicity, and have adhesiveness to be attached to the skin. The opening 315 may be smaller or larger than the opening unit 345, and may have the same size as that of the opening unit 345. The size of the opening 315 influences on the amount of sweat supplied to the sweat absorbing layer 340 (density of sweat glands x area =the number of sweat glands), so that the relative size of the opening 315 with respect to the size of the opening unit 345 may be determined according to the use environment and condition.

The second support layer 320 may be configured to cover and block the opening unit 345 of the sweat absorbing layer 340. Further, the second support layer 320 may include a polymer material having hydrophobicity, and a region corresponding to the plurality of opening units 345 may be formed to be transparent at least.

Figure 2:
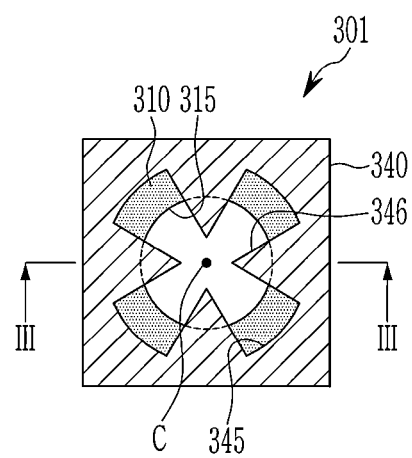
FIG. 2 is a top plan view illustrating a unit cell of the perspiration mapping patch according to the exemplary embodiment.
Figure 3:
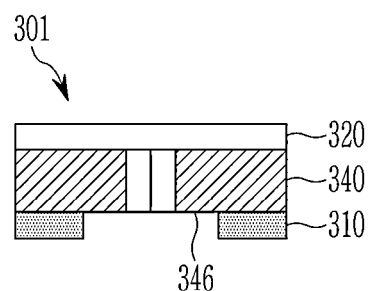
FIG. 3 is a cross-sectional view of the unit cell of the perspiration mapping patch illustrated in FIG. 2 taken along line III-III.

FIG. 2 is a top plan view illustrating a unit cell of the perspiration mapping patch according to the exemplary embodiment, and FIG. 3 is a cross-sectional view of the unit cell of the perspiration mapping patch illustrated in FIG. 2 taken along line 111-111.

Referring to FIG. 2, each of the plurality of opening units 345 may have a protrusion 346 extendable in a planar direction. The protrusion 346 may be configured to protrude into the opening 315 of the first support layer 310. In this case, at least a pair of protrusions 346 may be disposed to face each other, and for example, four protrusions 346 may be disposed at an interval of 90° with respect to a center C of the opening unit 345.

The protrusion 346 may be formed to be tapered as the protrusion 346 approaches the center C of the opening unit 345. That is, each protrusion 346 may have a tip that is sharpened toward the end, and the protrusions 346 opposing each other may be disposed so that the tips face each other with respect to the center C of the opening unit 345. The protrusion 346 configured as described above may be extended while having directionality when the protrusion 346 absorbs sweat and is expanded, and thus, the degree of deformation of the opening unit 345 may be more easily detected.

The protrusion 346 may be made of the same material as that of the sweat absorbing layer 340, and may be integrally formed by patterning the opening unit 345 of the sweat absorbing layer 340. The sweat absorbing layer 340 may be made of a material which is easily expanded when absorbing sweat, and may include, for example, a hydrogel. When the sweat absorbing layer 340 absorbs sweat, the sweat absorbing layer 340 may be expanded, and in this case, the protrusion 346 of the opening unit 345 of the sweat absorbing layer 340 may be extended in a direction facing the center of the opening unit 345. Further, the sweat absorbing layer 340 may control the degree and the direction of extension according to the absorption of the sweat by adjusting the shape and the size of the protrusion 346.

Figure 4:
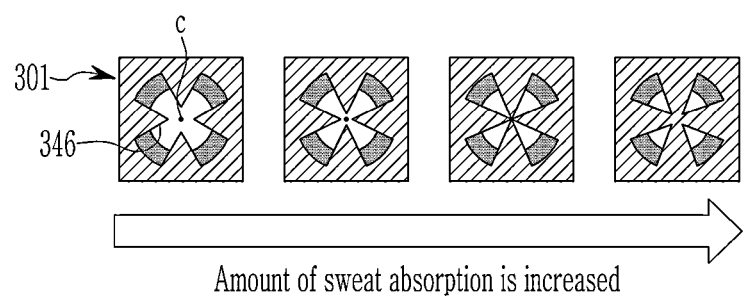
FIG. 4 is a top plan view illustrating a change in an opening unit of a unit cell according to an increase in the amount of sweat absorption (the amount of sweat secretion) in the perspiration mapping patch according to the exemplary embodiment.

FIG. 4 is a top plan view illustrating a change in a unit cell opening unit according to an increase in the amount of sweat absorption (the amount of sweat secretion) in the perspiration mapping patch according to the exemplary embodiment, Referring to FIG. 4, the perspiration mapping patch 30 according to the present exemplary embodiment is made of a material which is expanded when absorbing sweat, and an opened area of the opening unit 345 is gradually decreased according to an increase in the amount of sweat absorption (the amount of sweat secretion). In this case, the protrusions 346 which are formed in the opening unit 345 and oppose each other may visually and identifiably indicate the deformation state of the opening unit 345 as the spaced gap therebetween is gradually reduced.

Figure 5:
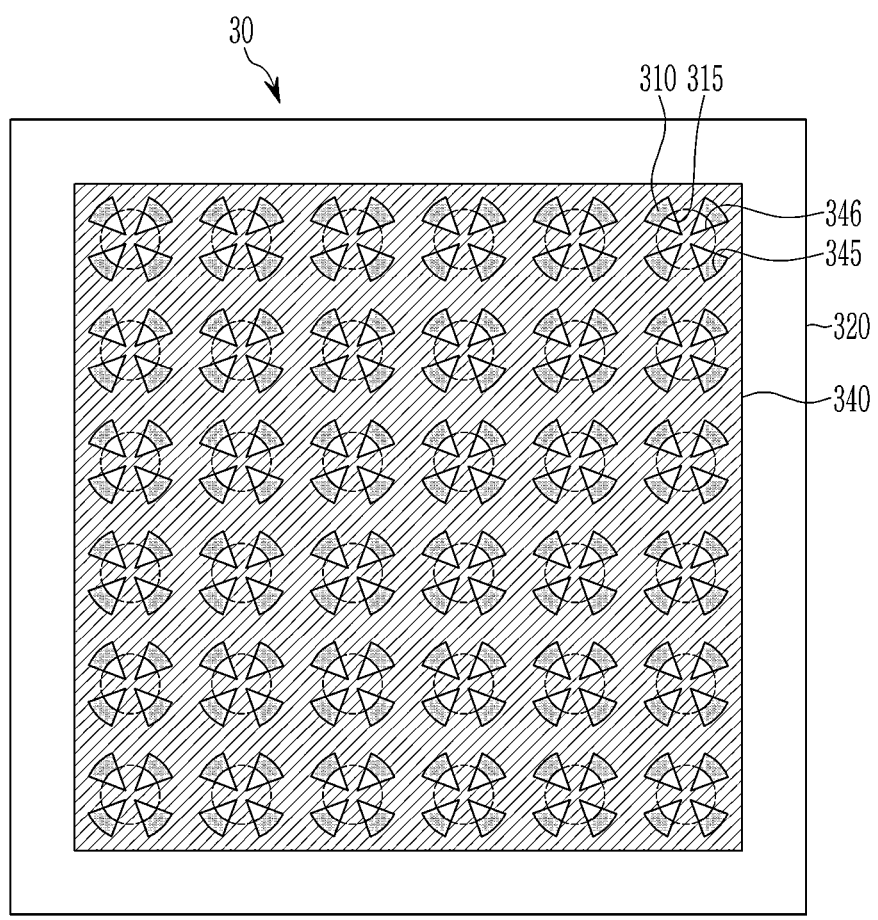
FIG. 5 is a top plan view illustrating the state where sweat is absorbed in the whole perspiration mapping patch according to the exemplary embodiment, so that a protrusion of the opening unit is deformed.
Figure 6:
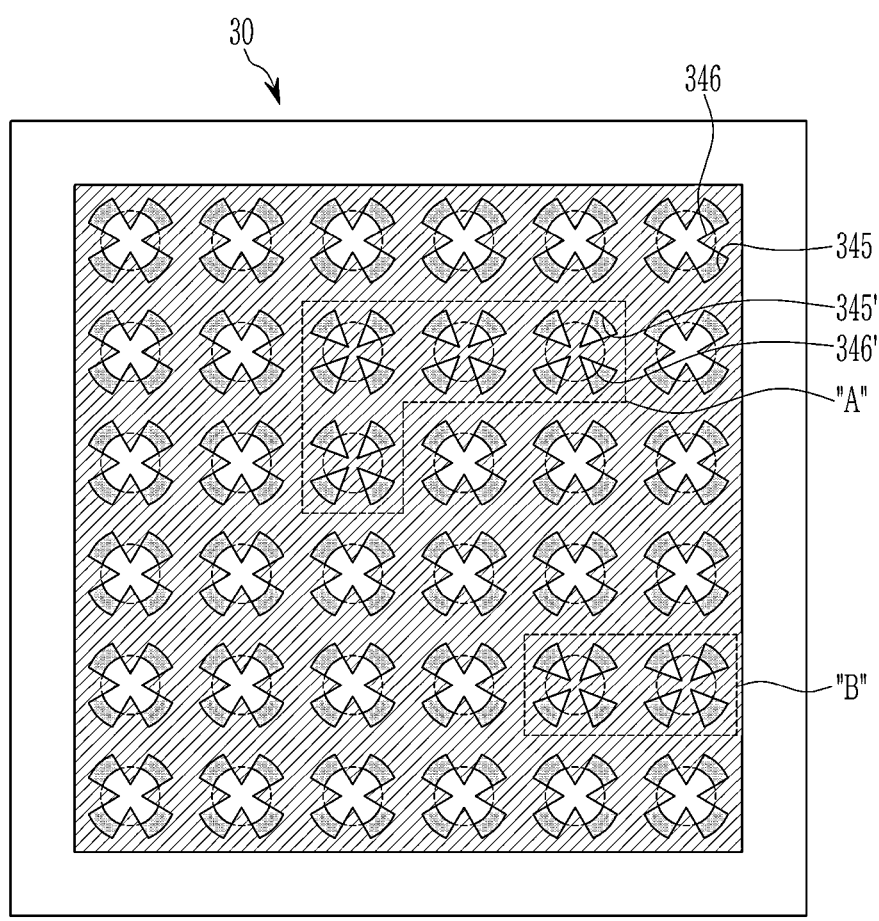
FIG. 6 is a top plan view illustrating the state where sweat is absorbed in a portion of the perspiration mapping patch according to the exemplary embodiment, so that a protrusion of the opening unit is deformed.

FIG. 5 is a top plan view illustrating the state where sweat is absorbed in the whole perspiration mapping patch according to the exemplary embodiment, so that a protrusion of the opening unit is deformed, and FIG. 6 is a top plan view illustrating the state where sweat is absorbed in a portion of the perspiration mapping patch according to the exemplary embodiment, so that a protrusion of the opening unit is deformed.

Referring to FIG. 5, when sweat is absorbed in the whole perspiration mapping patch 30 according to the present exemplary embodiment and the sweat absorbing layer 340 is expanded, it may be detected that the opening area is reduced as the protrusion 346 is extended in each opening unit 345.

In the meantime, when sweat is absorbed in the portion of the perspiration mapping patch 30 according to the present exemplary embodiment or a part of the perspiration mapping patch 30 has a relatively large amount of sweat absorption (the amount of sweat secretion), the degree of expansion of the sweat absorbing layer 340 may be differently exhibited depending on the part.

Referring to FIG. 6, the opening area is decreased while the protrusion 346 of the opening unit 345 is extended in two separately divided portions (area "A" and "B"), and the original state is maintained in other areas. Accordingly, it may be detected that the amount of sweat absorption (the amount of sweat secretion) is large in area "A" and area "B" in which the opening area is reduced.

Figure 7:
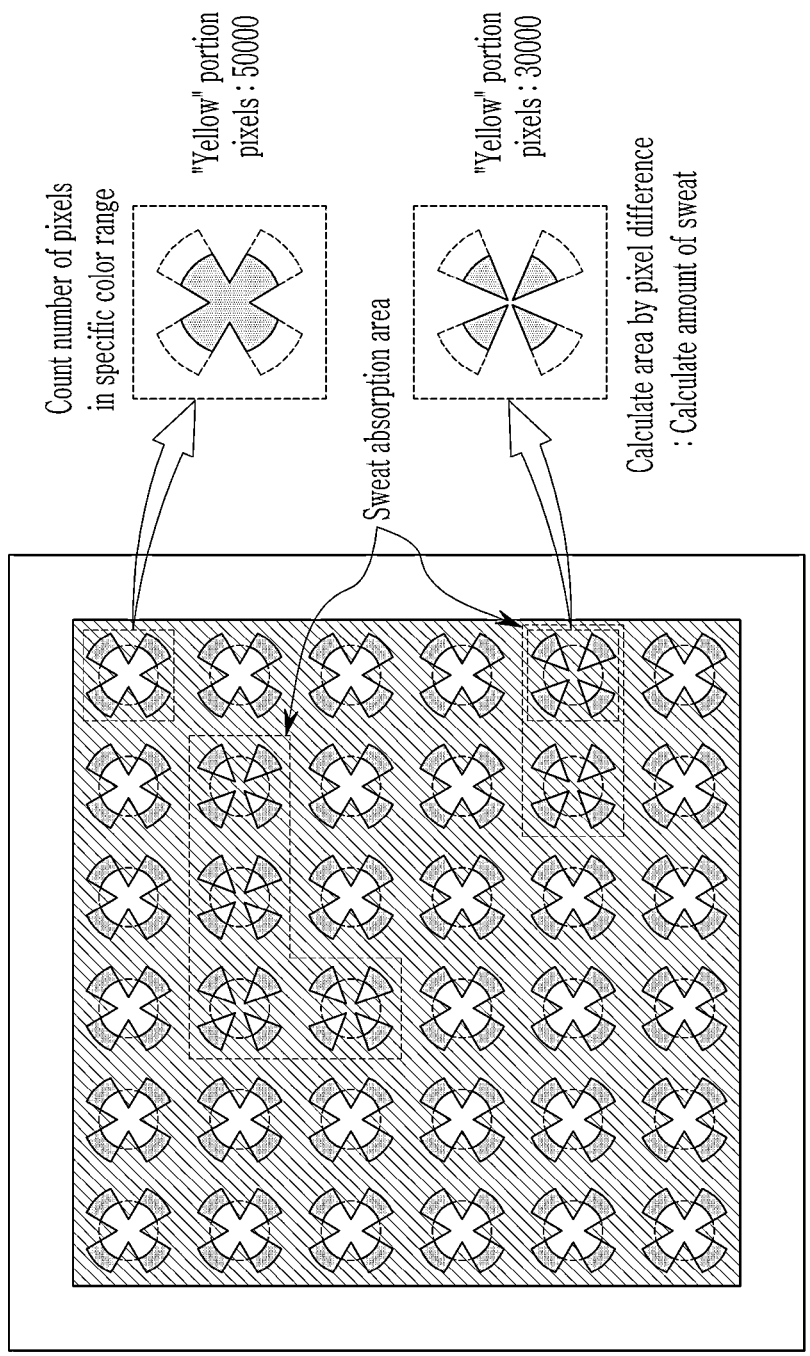
FIG. 7 is a diagram for describing a method of analyzing the degree of sweat absorption (secretion) of the area of the portion in the perspiration mapping patch illustrated in FIG. 6 which absorbs sweat and is deformed.

FIG. 7 is a diagram for describing a method of analyzing the degree of sweat absorption (secretion) of the area of the portion in the perspiration mapping patch illustrated in FIG. 6 which absorbs sweat and is deformed.

When sweat is absorbed in the portion of the perspiration mapping patch 30 illustrated in FIG. 6, or a portion of the perspiration mapping patch 30 relatively has the large amount of sweat absorption (the amount of sweat secretion), the degree of expansion of the sweat absorbing layer 340 is differently exhibited depending on the part, and the perspiration mapping patch 30 may be divided into sweat absorption areas (area "A" and "B") and non-absorption areas (the areas other than area "A" and "B"). That is, in the sweat absorption area, the opening area is reduced as the protrusion 346 of the opening unit 345 is extended, and the opening area is maintained in an initial state in the non-absorption area.

Herein, in order to identify the sweat absorption area and calculate the amount of sweat absorption (the amount of sweat secretion), an image analysis of obtaining an image of the perspiration mapping patch 30 and recognizing the degree of change of the image may be utilized. For example, for the image analysis, a smart phone application may be utilized, or an image may be obtained through a camera and a computing device may analyze the obtained image.

An opening area of the opening unit 345 in an image of a unit cell 301 of the perspiration mapping patch 30 may be an area of a portion that is not covered with the sweat absorbing layer 340 and the first support layer 310. When the perspiration mapping patch 30 is attached to the skin of the user, a color of the skin may be exposed through the portion that is not covered by the sweat absorbing layer 340 and the first support layer 310. Accordingly, when the color of the area through which the skin is exposed is yellow, the number of pixels corresponding to the yellow area may be calculated from the obtained image. In this case, the sweat absorbing layer 340 and the first support layer 310 are manufactured by selecting a color which is easily distinguished from the color of the exposed skin, so that the changing opening area of the opening unit 345 may be easily distinguished.

For example, referring to FIG. 7, when the number of pixels corresponding to the non-absorption area of the perspiration mapping patch 30 or the number of pixels corresponding to the opening area in the unit cell 301 in the initial state is 50,000 and the number of pixels corresponding to the opening area in the unit cell 301 in the sweat absorption area is 30,000, the difference in the pixel number may be calculated as the area corresponding to the amount of sweat absorption (the amount of sweat secretion). In this case, when the amount of sweat absorption of the sweat absorbing layer 340 according to the number of pixels is preset and then the changed number of pixels is calculated, the calculated number of pixels may be converted into the amount of sweat absorption to be output.

For another example, the entire sweat absorbing layer 340 may be configured to have a color, and the first support layer 310 and the second support layer 320 may be made transparent, and in this case, the amount of sweat absorption may be calculated and output based on an opened area of the sweat absorbing layer 340.

Figure 8:
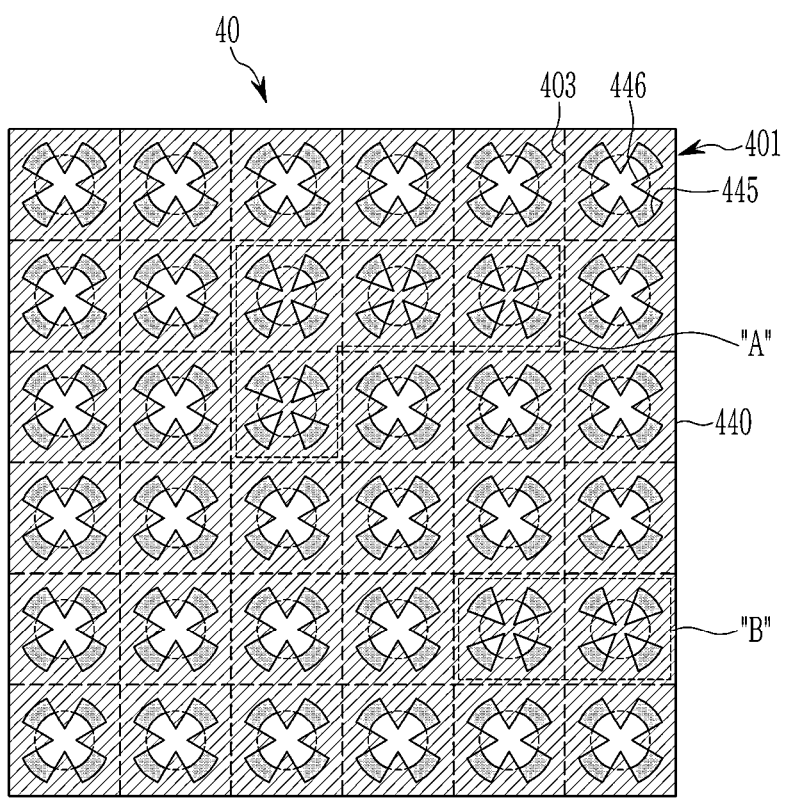
FIG. 8 is a top plan view illustrating the state where sweat is absorbed in a portion of a perspiration mapping patch according to another exemplary embodiment, so that the protrusion of the opening unit is deformed.
Figure 9:
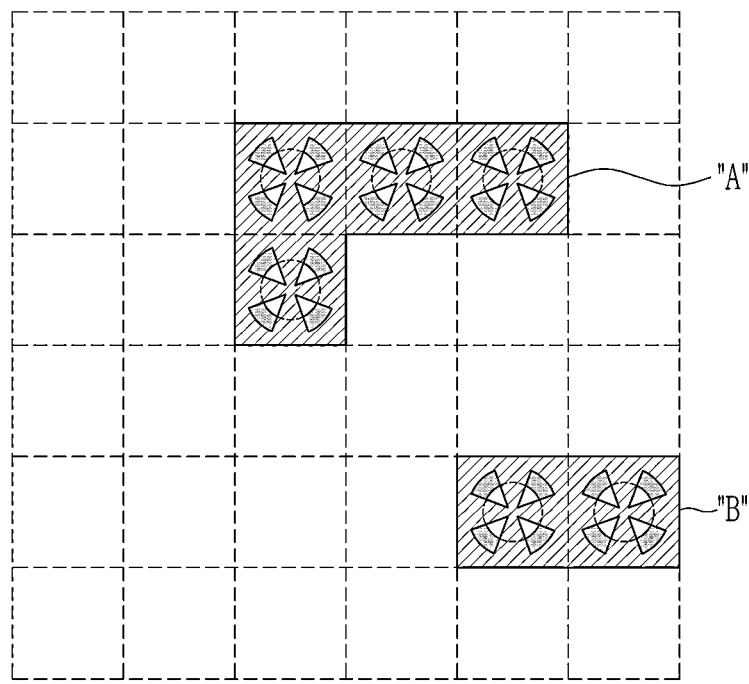
FIG. 9 is a top plan view illustrating the state where the perspiration mapping patch illustrated in FIG. 8 is torn off while only the portion in which sweat is absorbed is left.

FIG. 8 is a top plan view illustrating the state where sweat is absorbed in a portion of a perspiration mapping patch according to another exemplary embodiment, so that the protrusion of the opening unit is deformed, and FIG. 9 is a top plan view illustrating the state where the perspiration mapping patch illustrated in FIG. 8 is torn off while only the portion in which sweat is absorbed is left, Referring to FIG. 8, a perspiration mapping patch 40 according to the present exemplary embodiment may be divided into a plurality of unit cells 401 and be perforated from each other. That is, a sweat absorbing layer 440 includes a plurality of unit cells 401 divided for the plurality of opening units 445, respectively, and the plurality of unit cells 401 may be divided by a perforation line 403 partially cut in advance so as to be perforated from each other. The plurality of unit cells 401 may be arranged in a lattice form, and an individual opening unit 445 may be located within each unit cell 401

When the perspiration mapping patch 40 according to the present exemplary embodiment exhibits the same distribution of the amount of sweat absorption (the amount of sweat secretion) illustrated in FIG. 6, an opening area is reduced as a protrusion 446 of the opening unit 445 is extended in the two separately divided portions (area "A" and "B"), and other areas maintain the original state.

In this case, when only the unit cells 401 in which the amount of sweat absorption (the amount of sweat secretion) is large are left and the remaining parts are perforated and removed, only the unit cells 401 corresponding to areas "A" and "B may be attached to the skin and left as illustrated in FIG. 9.

FIGS. 10 to 13 are top plan views illustrating unit cells of perspiration mapping patches according to other exemplary embodiments. The perspiration mapping patch according to another exemplary embodiment may include various forms of protrusion.

Figure 10:
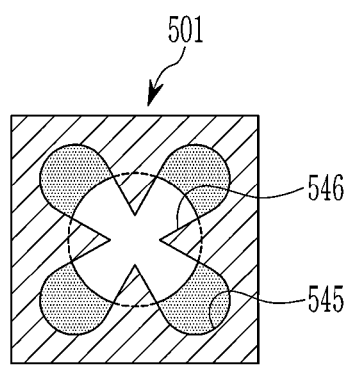
FIGS. 10 to 13 are top plan views illustrating unit cells of perspiration mapping patches according to other exemplary embodiments.
Figure 11:
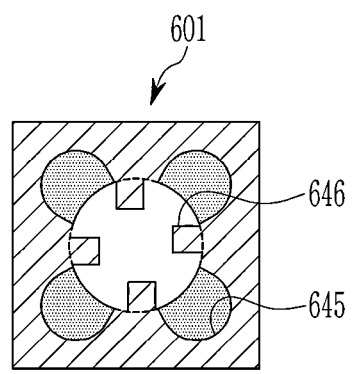
Figure 12:
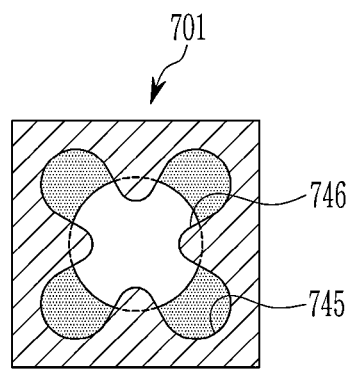

Referring to FIGS. 10 to 12, protrusions 546 and 646 of opening units 545 and 645 in unit cells 501 and 601 of the perspiration mapping patches may have tips (FIG. 10) that become sharper toward the end or a rectangular plane (FIG. 11), and for another example, in the case where the protrusions 546 and 646 have a rectangular plane, the areas of the protrusions 546 and 646 may be hierarchically formed differently as the protrusions 546 and 646 are away from the centers of the opening units. Further, a protrusion 746 of an opening unit 745 in a unit cell 701 of the perspiration mapping patch may be formed of a rounded protrusion (FIG. 12).

Figure 13:
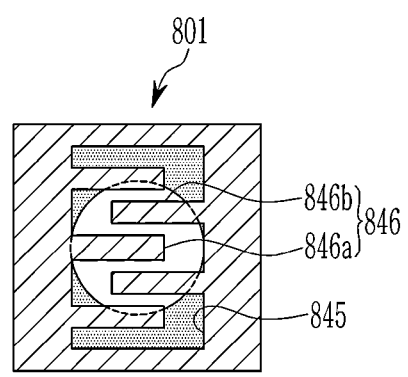

Referring to FIG. 13, in a protrusion 846 of an opening unit 845 in each unit cell 801 of a perspiration mapping patch, a pair of protrusions 846a and 846b extending alternately may be disposed in an opening of a first support layer.

Hereinafter, the process of manufacturing the perspiration mapping patch, and the result of the evaluation of a sweat detection characteristic by using the manufactured perspiration mapping patch will be described in more detail through an illustrative example. However, it should be noted that the protection scope of the present invention is not intended to be limited to the following example.

Manufacture Perspiration Mapping Patch

Example 1

Perspiration Mapping Patch Including Circular Opening Unit

Figure 14:
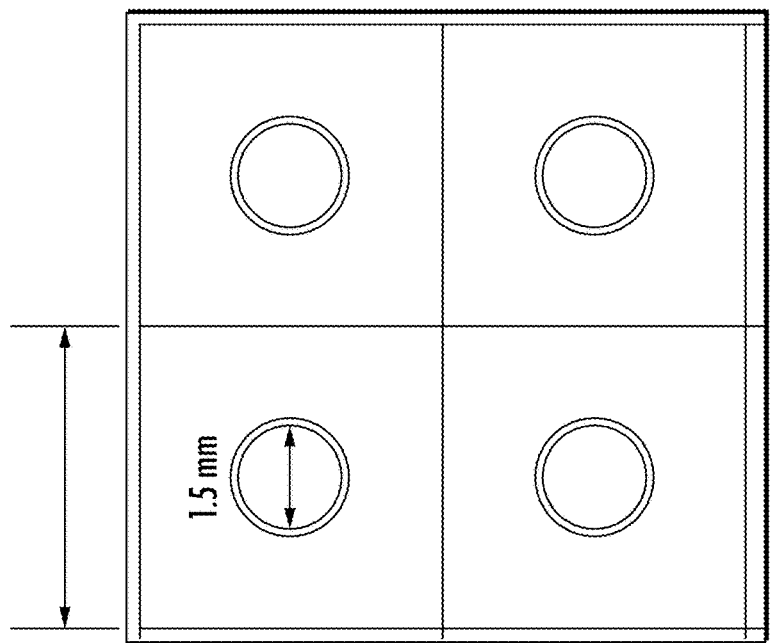
FIG. 14 is a drawing of a film mask used in manufacturing the perspiration mapping patch including a circular opening unit and a picture of a manufactured hydrogel.
Figure 14:
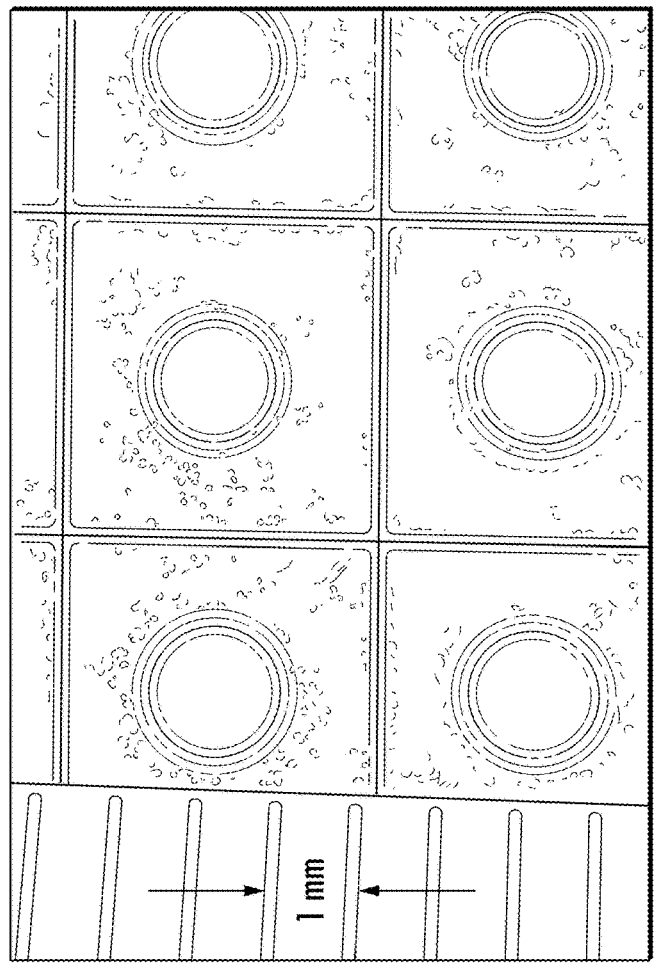

An acrylic acid and acrylamide-based hydrogel solution was prepared, and then photo-cured with UV on a film mask including a circular pattern to manufacture a hydrogel with the pattern. In particular, 1.32 g of KOH was added to 3.14 mL of distilled water and then 5.76 mL of acrylic acid was added and mixed. 1.66 mL of an acrylamide/bis-acrylamide solution was added to the mixed solution and mixed. Herein, 0.65 mL of an N-vinylpyrrolidone/Irgacure 651 solution was added and mixed, and then 12 mL of glycerol was added. A film mask having circular opening units was placed on the prepared hydrogel solution and the hydrogel solution was photo-cured with UV for 30 seconds and then washed. The transparent hydrogel was colored with blue in order to easily analyze a change in an opened area by using a camera. A drawing of the film mask with the circular pattern used for the photo-curing and a picture of the manufactured hydrogel are represented in FIG. 14.

Example 2

Figure 15:
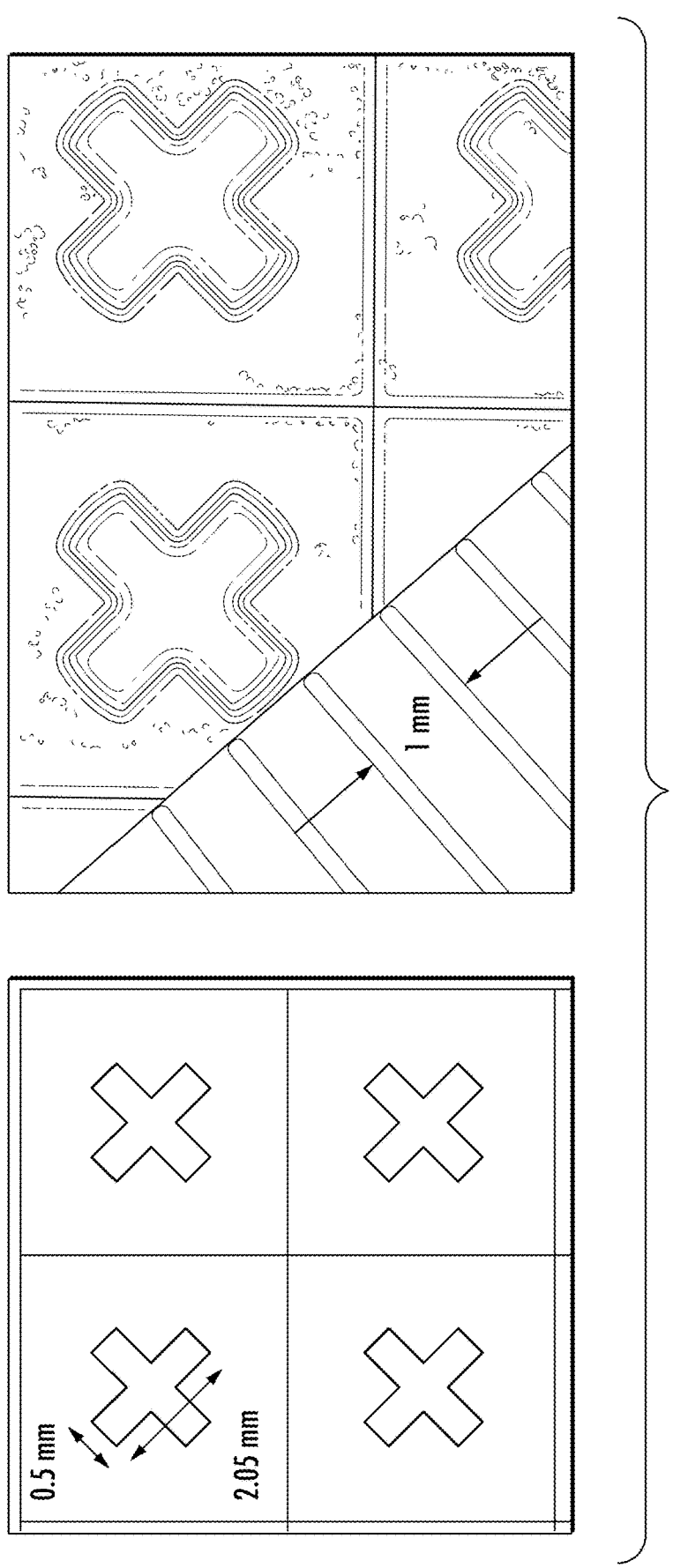
FIG. 15 is a drawing of a film mask used for manufacturing a perspiration mapping patch in which an opening unit has a protrusion protruding in a plane direction, and a picture of the manufactured hydrogel.
Figure 16:
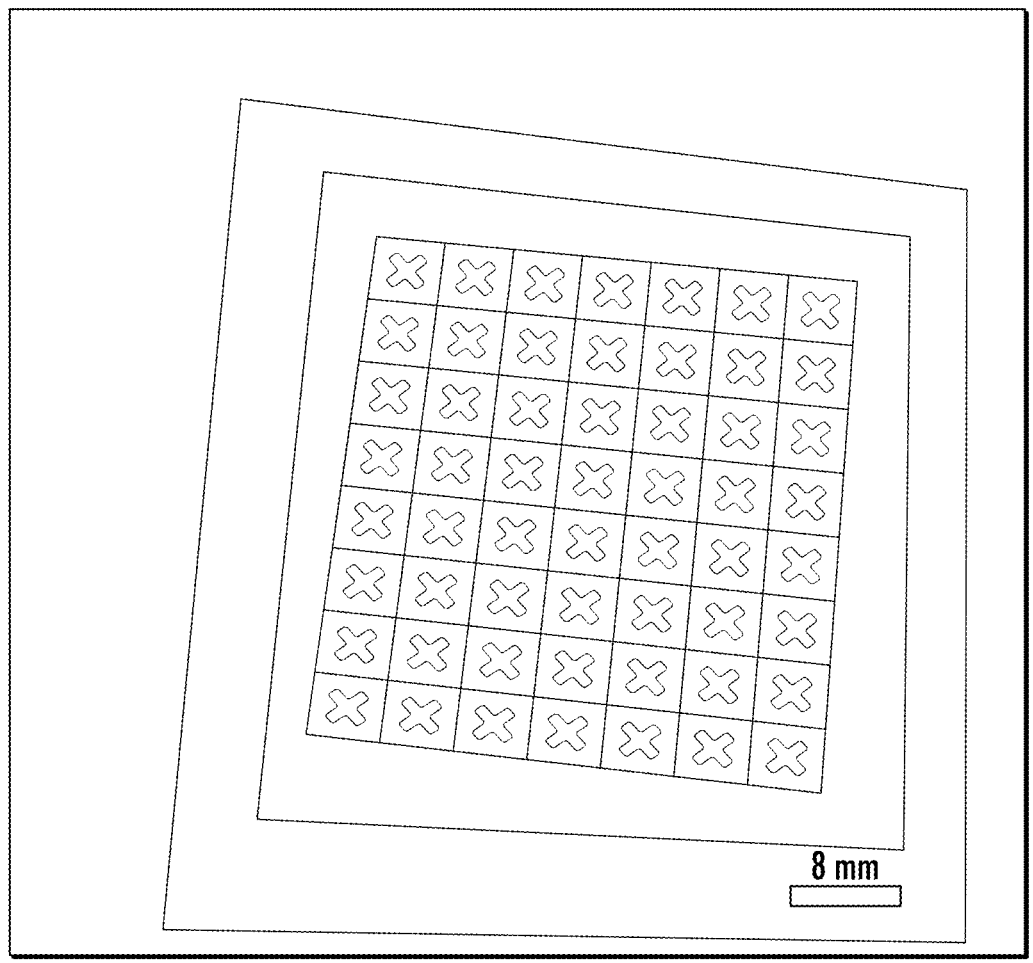
FIG. 16 is a picture showing the perspiration mapping patch including opening units in which openings have protrusions protruding in a plane direction are manufactured in a 7×7 array.

Perspiration Mapping Patch Including Protrusions in Which Openings are Extendable in a Plane Direction An acrylic acid and acrylamide-based hydrogel solution was prepared, and then photo-cured with UV on a film mask patterned with openings protruding in the shape of a cross to manufacture a hydrogel with the pattern. Except for the pattern shape, the manufacturing method is the same as that of Example 1. A drawing of the film mask used for the photo-curing and a picture of the manufactured hydrogel are represented in FIG. 15. A picture of the perspiration mapping patch in which the units including the opening units protruding in the shape of a cross are disposed in a 7×7 array is represented in FIG. 16.

Evaluation Example

1. Evaluation of Sweat Detection Characteristic of Example 1

Figure 17:
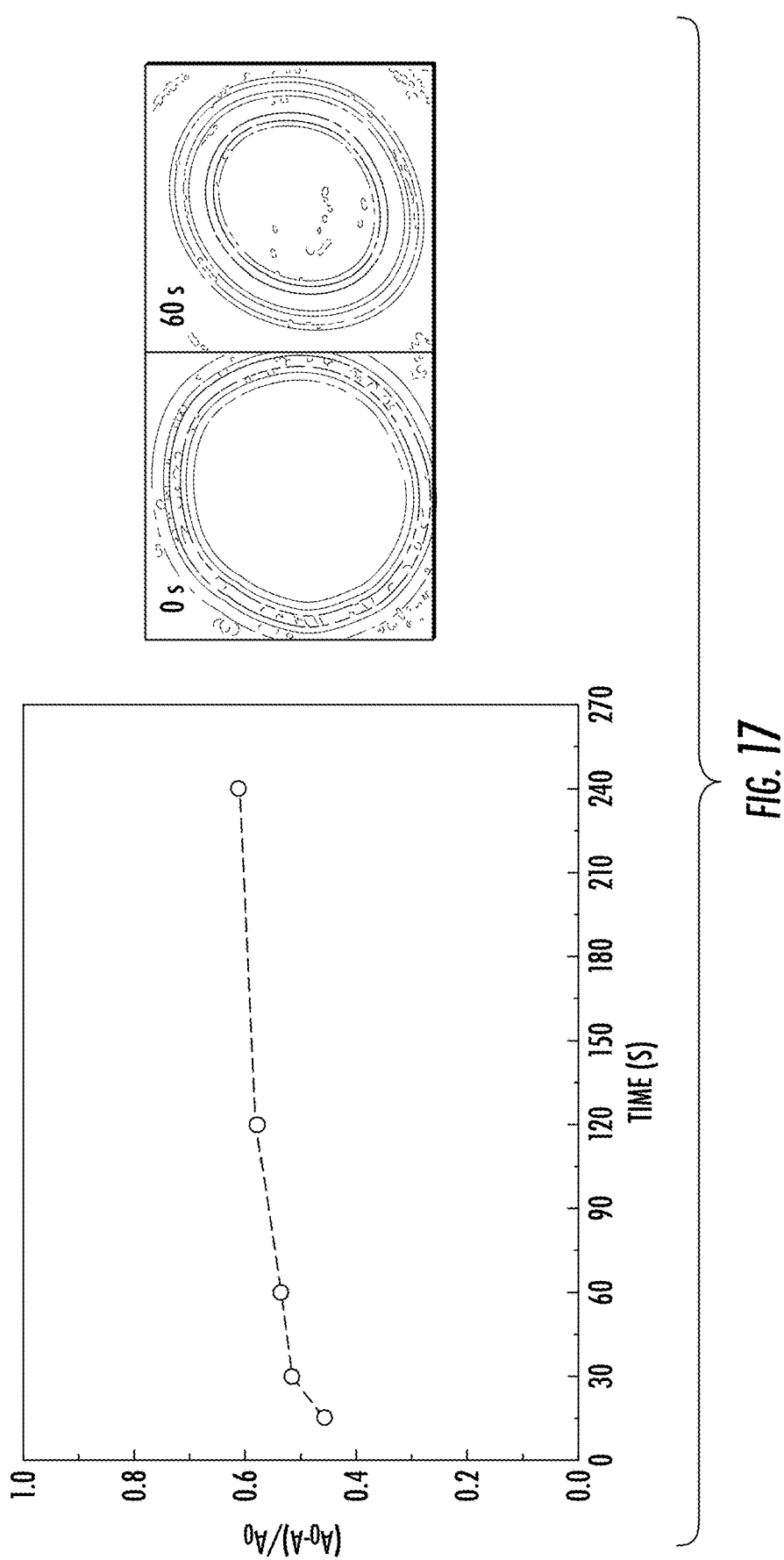
FIG. 17 is a graph illustrating a change in a shape and an opened area of an opening unit according to sweat absorption of a sweat absorbing layer including a circular opening unit.

After 1 μL of 100 mM NaCl solution was dropped on the hydrogel including the circular opening units, a change in an opened area of the opening unit was measured over time, and the results are shown in FIG. 17. In the case of the circular opening unit, it can be seen that about 50% of the original opened area (Au) of the opening unit is closed within 30 seconds. Accordingly, it can be seen that it is possible to sensitively detect sweat discharge by using the circular opening unit.

2. Evaluation of Sweat Detection Characteristic of Example 2

Figure 18:
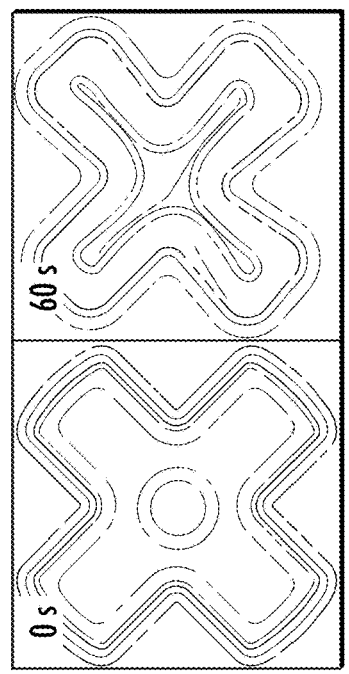
FIG. 18 is a graph illustrating a change in a shape and an opened area of an opening unit according to sweat absorption of a sweat absorbing layer in which an opening unit has a protrusion protruding in a plane direction.
Figure 18:
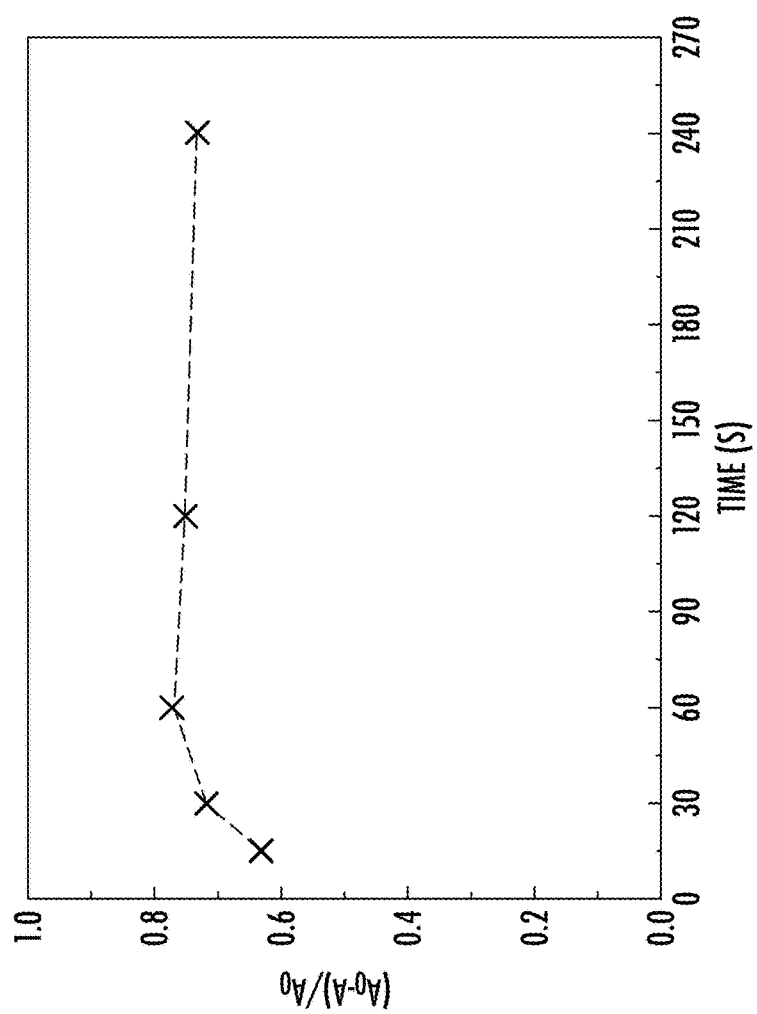

After 1 μL of 100 mM NaCl solution was dropped on the hydrogel in which the opening unit includes the protrusion protruding in a plane direction, a change in an opened area of the opening unit was measured over time, and the results are shown in FIG. 18. In the case of the protruding opening unit, it can be seen that about 60% of the original opened area (Au) of the opening unit is already closed in about 15 seconds, and 70% or more of the original opening area is closed after 30 seconds. Accordingly, it can be seen that the opening unit including the protruding protrusion is capable of more sensitively detecting sweat than the circular opening unit.

Although the exemplary embodiment of the present invention has been described above, the present invention is not limited thereto, and it is possible to carry out various modifications within the scope of the claims, the description of the invention, and the accompanying drawings, and it is apparent that this also belongs to the scope of the present invention.

DESCRIPTION OF SYMBOLS

30, 40: perspiration mapping patch
301, 401, 501, 601, 701, 801: unit cell
310: first support layer
315: opening
320: second support layer
340, 440: sweat absorbing layer
345, 445, 545, 645, 745: opening unit
346, 446, 546, 646, 746, 846: protrusion
403: perforated line

What is claimed is:

1. A perspiration mapping patch configured to be attached to skin of a user to absorb sweat and defining a stacking direction and a plane direction orthogonal to the stacking direction, the perspiration mapping patch comprising:
   a sweat absorbing layer in which a plurality of opening units is arranged;
   a first support layer which is stacked on a first surface of the sweat absorbing layer along the stacking direction and includes an opening opened to correspond to each of the plurality of opening units; and
   a second support layer stacked on a second surface facing an opposite side of the first surface of the sweat absorbing layer,
   wherein each of the plurality of opening units comprises a first portion that overlaps the opening of the first support layer along the stacking direction and a second portion that does not overlap the opening of the first support layer along the stacking direction, and
   wherein each of the openings of the first support layer comprises a third portion that does not overlap the opening units of the sweat absorbing layer along the stacking direction.

2. The perspiration mapping patch of claim 1, wherein:
   each of the plurality of opening units includes a protrusion that extends in the plane direction.

3. The perspiration mapping patch of claim 2, wherein:
   the protrusion is configured to protrude into the opening of the first support layer.

4. The perspiration mapping patch of claim 2, wherein:
   at least one pair of protrusions is disposed to face each other.

5. The perspiration mapping patch of claim 2, wherein:
   the protrusion is formed to be tapered as the protrusion approaches a center of each of the opening units.

6. The perspiration mapping patch of claim 2, wherein:
   at least one pair of protrusions extended alternately is disposed in the opening.

7. The perspiration mapping patch of claim 1, wherein:
   the first support layer includes a material having hydrophobicity.

8. The perspiration mapping patch of claim 1, wherein:
   the first support layer is configured to have adhesiveness.

9. The perspiration mapping patch of claim 1, wherein:
   the second support layer includes a material having hydrophobicity.

10. The perspiration mapping patch of claim 1, wherein:
    in the second support layer, at least an area corresponding to each of the plurality of opening units is formed to be transparent.

11. The perspiration mapping patch of claim 1, wherein:
    the plurality of opening units is formed to have a matrix array.

12. The perspiration mapping patch of claim 1, wherein:
    the first surface of the sweat absorbing layer is configured to face the skin.

13. The perspiration mapping patch of claim 1, wherein:
    the second support layer is configured to cover and block the opening unit of the sweat absorbing layer.

14. The perspiration mapping patch of claim 1, wherein:
    the sweat absorbing layer includes a hydrogel.

15. The perspiration mapping patch of claim 1, wherein:
    the sweat absorbing layer is configured to have a color.

16. The perspiration mapping patch of claim 1, wherein:
    the sweat absorbing layer is divided into a plurality of unit cell by perforation lines, each of the unit cells including one of the plurality of opening units, and
    the plurality of unit cells is configured to be perforated from each other.

17. The perspiration mapping patch of claim 1, wherein:
    each of the openings is a circular opening having a perimeter, and
    the second portion of each of the opening units extends outside the perimeter of the opening in the plane direction.

* * * * *